United States Patent
Flückiger

(12) 
(10) Patent No.: US 6,620,142 B1
(45) Date of Patent: Sep. 16, 2003

(54) DISPOSABLE URINARY AID

(76) Inventor: Werner Flückiger, Kreuzbüntenstrasse 713, CH-5727 Oberkulm (CH)

( * ) Notice: Subject to any disclaimer, the term of this patent is extended or adjusted under 35 U.S.C. 154(b) by 0 days.

(21) Appl. No.: 09/830,199

(22) PCT Filed: Aug. 18, 2000

(86) PCT No.: PCT/CH00/00440

§ 371 (c)(1), (2), (4) Date: Apr. 23, 2001

(87) PCT Pub. No.: WO01/13831

PCT Pub. Date: Mar. 1, 2001

(30) Foreign Application Priority Data

Aug. 24, 1999  (EP) .......................... 99810757

(51) Int. Cl.⁷ .................................. A61F 5/44
(52) U.S. Cl. ...................... 604/349; 604/355
(58) Field of Search .................. 604/347, 349–353, 604/346, 355, 317, 385.01

(56) References Cited

U.S. PATENT DOCUMENTS

| | | | |
|---|---|---|---|
| 4,202,058 A | * 5/1980 | Anderson | 4/144.3 |
| 4,296,502 A | 10/1981 | Bortle | |
| 4,937,890 A | 7/1990 | Tafur | |
| 5,300,052 A | * 4/1994 | Kubo | 4/144.1 |
| 5,722,136 A | 3/1998 | Jonec | |
| 5,797,147 A | * 8/1998 | Young et al. | 137/515 |
| 5,961,501 A | * 10/1999 | Cassidy et al. | 604/317 |

FOREIGN PATENT DOCUMENTS

| | | |
|---|---|---|
| DE | 3722863 | 3/1988 |
| DE | 4343789 | 5/1995 |

* cited by examiner

*Primary Examiner*—Weilun Lo
*Assistant Examiner*—C L Anderson
(74) *Attorney, Agent, or Firm*—Sidley Austin Brown & Wood, LLP

(57) ABSTRACT

The aid includes at least one hose-like conduit element (1) having walls (2, 3) made of absorbent hygienic paper which bound a conduit channel (4) for urine. The conduit element (1) comprises a first end section (A) having an inlet part (5) positionable at the body of a respective user and a second end section (B) having an outlet part (6) to channel the urine. The first end section (A) is formed by first wall parts (2a and 3a) which are provided with a wetting inhibiting coating (18) at the inner sides. The second end section (B) is formed by second wall parts (2b and 3b) free of wetting inhibiting agent. The first end section (A) is designed with a gripping part (7) protruding to the side which is formed by tongue-like protrusions (12) of the first wall parts (2a and 3a).

This embodiment allows a comfortable, hygienically advantageous use of the aid and a fast softening and/or dissolving of the used conduit element (1) in the water of a toilet.

5 Claims, 2 Drawing Sheets

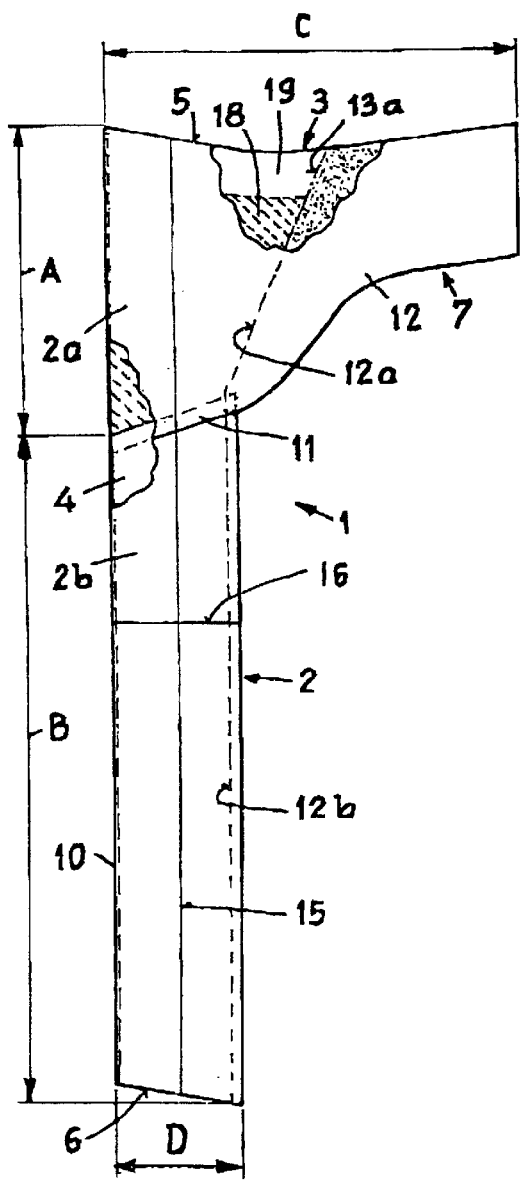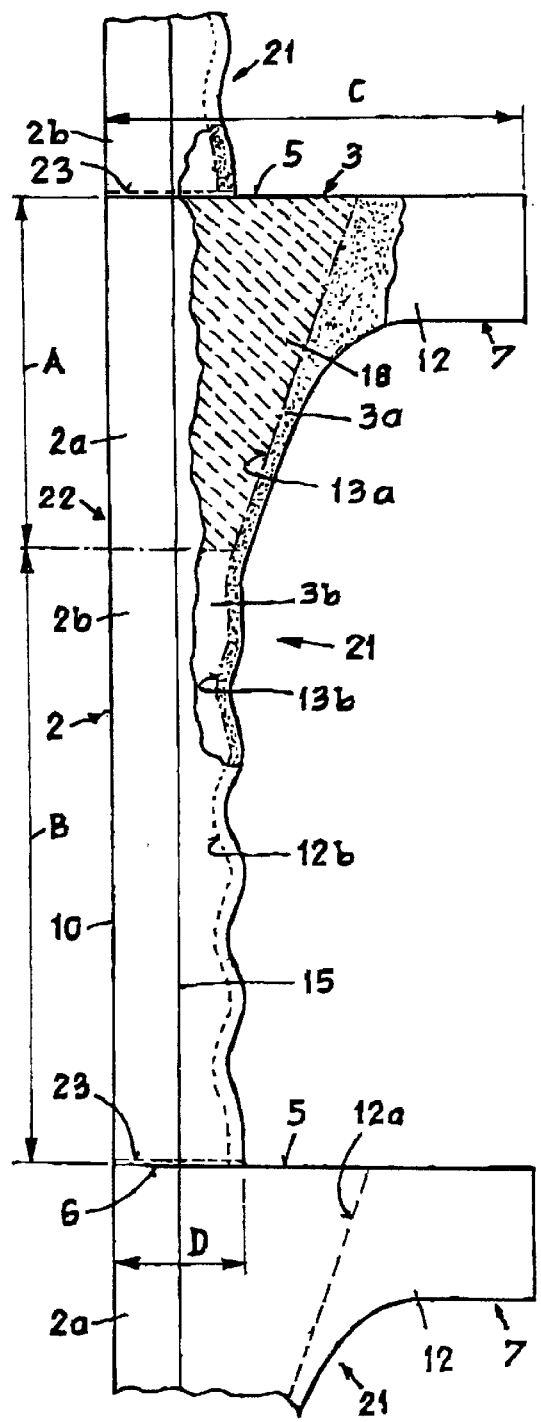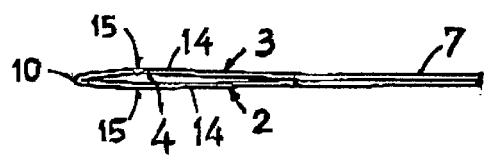

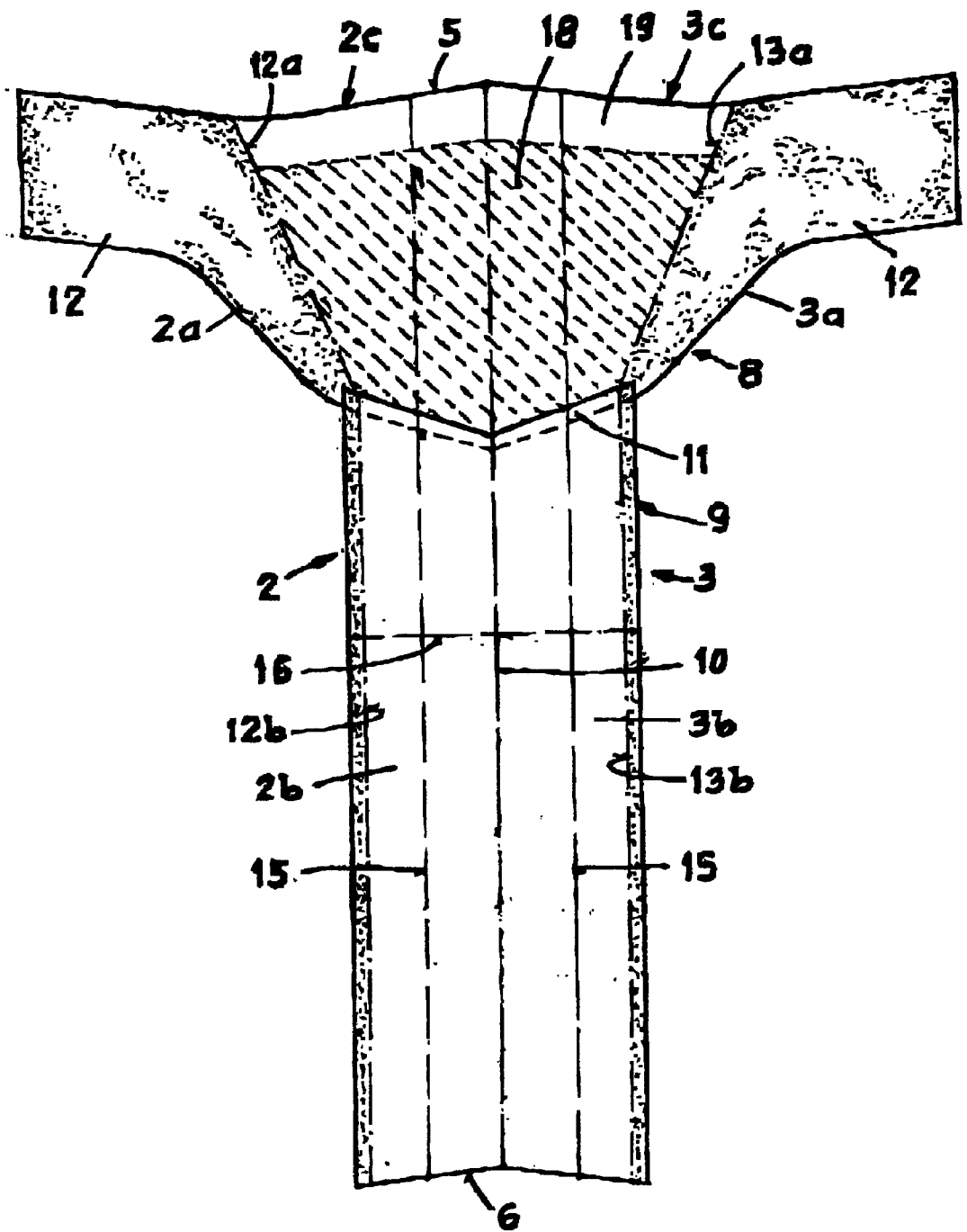

DISPOSABLE URINARY AID

The invention relates to a disposable aid for urination in accordance with the preamble of claim 1.

An aid of the said kind for male users known from U.S. Pat. No. 5,722,136 includes a plurality of conduit elements which have a sleeve-like inlet part and an outlet part intended to be immersed into the water of a toilet bowl. The conduit elements are formed in each case from two plies of paper whose width corresponds approximately to the width of a roll of toilet paper. The plies of paper are connected to one another at their two side edges and bound a conduit channel which is provided over its whole length with a waterproof coating.

The known conduit elements have a relatively large longitudinal dimension which should optionally be matched to the body size of the respective user by tearing off one or more longitudinal segments to ensure a direct channelling of the urine into the water filling of the toilet. When these conduit elements are dropped into the water filling after use, there is a risk that the relatively wide-area plies of paper, which are coated over their whole length, may block the toilet since the softening or dissolving of the paper material is delayed by the coating and thus the obstruction-free flushing of the conduit elements can be hindered.

The invention has the underlying object of providing an aid of the kind initially mentioned which is improved, particularly in this respect, and which is easier to handle.

This object is satisfied in accordance with the invention with the features of claim 1.

The aid formed in accordance with the invention includes a conduit element improved with respect to previous designs in a simple embodiment which ensures a hygienically clean handling in use and a softening and/or dissolving of a respectively used conduit element which is accelerated with respect to previous designs.

Advantageous embodiments of the invention result from the dependent claims.

The invention is explained in the following with reference to the enclosed drawing, in which are shown:

FIG. 1 a side view of a disposable aid designed in accordance with the invention for urination for male users;

FIG. 2 the aid of FIG. 1 in a plan view;

FIG. 3 the aid of FIG. 1 in an inner view unfolded in the drawing plane; and

FIG. 4 a side view of an aid in accordance with the invention according to a different embodiment.

The aid in accordance with FIGS. 1–3 includes a plurality of flexible, hose-like conduit elements 1, of which only one is shown. The conduit elements 1 serve to simplify urination in a standing position of the respective user and to channel urine into a toilet (not shown). The aid is suitable in particular for use in private or other toilets, e.g. such of means of transport, in which no urinal is available.

The conduit element 1 is formed by two walls 2 and 3 which can be conjoined in a flat manner, which are made of absorbent toilet paper which is softenable and/or degradable in water and which bound a conduit channel 4 through which urine can flow. The conduit element 1 comprises a first end section A having an inlet part 5 formed to receive the penis which can be placed at the body of the respective user and a second section B having an outlet part 6 which can be oriented with respect to a toilet to channel the urine.

The conduit element 1 is executed with a gripping part 7 which is formed at the first end section A, projects to the side from the region of the conduit channel 4, and is shaped like a pistol grip. A comfortable and advantageously hygienic handling of the aid is accordingly ensured. In accordance with FIG. 1, the first end section A is designed with a width C which can, for example, correspond to the width of a roll of toilet paper, while the second end section B has a width D which corresponds to a fraction, in accordance with the illustration approximately a third, of the width C. The conduit element 1 therefore consists of sections of the paper material with a relatively small area whose softening and/or dissolving requires an advantageously short duration of the used conduit element 1 in the water of the toilet.

As can be seen in particular from FIG. 3, the walls 2 and 3 of the conduit element 1 shown in an unfolded manner are provided with a longitudinal fold 10 which can be oriented in the longitudinal direction of said conduit element 1 and which is executed symmetrically for this purpose. The walls 2 and 3 are formed in the first end section A by two first wall parts 2a and 3a, and in the second end section B by two second wall parts 2b and 3b. Tongue-like protrusions 12 are formed at the first wall parts 2a and 3a and each form half of the gripping part 7.

The end sections A and B can be formed by segments of a wall part formed as one piece or, as illustrated, by segments of a first wall part 8 and of a second wall part 9 connected thereto via a connection position, e.g. via an adhesive edge. The wall parts 2a and 3a or 2b and 3b respectively can be folded around the longitudinal fold 10 and can be connected to one another at a distance from it, in order to form the conduit channel 4, via side edge regions 12a and 13a or 12b and 13b respectively which can be brought together and which are indicated in the drawing by chain-dotted border lines.

The edge regions which can be brought together can be connected to one another in each case by a mechanical arrangement, e.g. in the form of intermeshing embossed features, or, as assumed in the example shown, by a bonding agent which can dissolve quickly in water. The edge regions 12a and 13a each extend over one of the tongue-like protrusions 12 and bound, with the longitudinal fold 10, two part segments 2c and 3c of the wall parts 2a and 3a which form the inner sides of the conduit channel 4 and extend divergently over the section A against the inlet part 5. The part segments 2c and 3c are provided with a coating 18 which is active for a brief period, which inhibits wetting and which is illustrated in the drawing as an area hatched with broken lines.

The coating 18 can extend over substantially the whole end section A or, as illustrated, be bound by a wiping edge 19 free of wetting agents provided in the region of the inlet part 5. Any residual urine possibly still present after the use of the conduit element 1 can be wiped off and removed in a hygienically advantageous manner with the appropriately absorbently formed wiping edge 19.

The coating 18 can be formed by an impregnation with a material, e.g. a soap, a fat or the like, which can be degraded in an environmentally friendly manner and which can dissolve and/or degrade rapidly on contact with water. The coating 18 can furthermore contain a medical test agent, e.g. an indicator, which reacts to the acid or base property of the urine of a respective user. Conduit elements 1 of such a design can therefore simultaneously be used as a simple means for appropriate medical control functions required daily, for example.

The edge regions 12b and 13b of the second wall parts 2b and 3b bound in the second end section B, together with the longitudinal fold 10, two inner wall parts of the conduit channel 4 free of wetting inhibiting agent. The conduit channel 4 is thus coated with the wetting inhibiting material only in the first end section A including the gripping part 7 and thus over a fraction, approximately the first third in accordance with the illustration, of the length of the conduit element 1, while the gripping part 7 and the wall parts 2b and 3b forming the second end section B are uncoated and thus made absorbent on both sides, Accordingly, much the greater part of the paper material of a respectively used conduit element 1 is softenable and/or degradable in an advantageously short time in the water of the toilet.

The second end section B formed in the form of a relatively narrow hose can furthermore be made relatively highly soggy from the inside in each case by the urine which flows through it. The own weight of end section B is increased accordingly so that it rapidly assumes a perpendicular draining position and so allows a controllable, directed outflow of the urine. The soaked end section B simultaneously effects a braking of the flow of the urine before this goes over into a remaining free fall. In this way, the conduit element 1 can be executed with a relatively small longitudinal dimension, e,g. one amounting to 40–50 cm, since a hygienically proper channelling of the urine can already be achieved when the outlet part 6 of the end section B is positioned at a distance above the water level in the upper edge region of a toilet bowl of a conventional design.

In the described embodiment, the decomposition process of the second end section B is further advanced in time with respect to the first end section A so that when the used conduit element 1 is dropped, only a correspondingly small amount of relatively dry paper material enters the water of the toilet, whereby a dissolving of the conduit element 1 can be achieved which is substantially improved with respect to previous embodiments.

As can be seen in particular from FIG. 2, the walls 2 and 3 can each be designed with an arch 14 which is at least approximately stable in shape and which extends transversely to the longitudinal extent of the conduit element 1, whereby the flat-folded conduit element 1 can be broadened with low effort and thus its use made easier. The arches 14 can be formed in accordance with the illustration by two longitudinal folds 15 which respectively extend over the wall parts 2a and 2b and 3a and 3b. The conduit element 1 can furthermore be provided with at least one transverse fold 16 extending transversely to the longitudinal extent of the conduit element 12 over the walls 2 and 3 and can be designed to fold around this. The conduit element 1 is accordingly stackable in the folded state and can be accommodated in a supply package (not shown) together with further conduit elements 1 each folded around a corresponding transverse fold 16. The conduit elements 1 can each be connected to a subsequent conduit element 1 in a manner where they can be folded into one another around the relevant transverse fold 16 and can be hooked to one another to form a loosely connected stack and from where they can be made available in a singly removable manner.

Parts corresponding to one another are shown with the same reference numerals in FIGS. 1 and 4. The aid in accordance with FIG. 4, whose design substantially corresponds to that of FIGS. 1–3, includes a plurality of flexible, hose-like conduit elements 21 which are detachably connected to one another and which can be made available in a supply package (not shown), e.g. on a supply roll, in a singly removable manner. FIG. 4 shows one of the conduit elements 21 in a partially cut away full view and two adjacent conduit elements 21 in a part view. In contrast to the design in accordance with FIGS. 1–3, the first and second wall parts 2a and 3a or 2b and 3b respectively of each conduit element 21 are formed at a single one-piece wall part 22 which extends over a detachable longitudinal section of a one-piece web of an absorbent hygienic paper which contains a plurality of such longitudinal sections.

The first wall parts 2a and 3a of the conduit elements 21 are each connected via a joint to the second wall parts 2b and 3b of the respectively adjacent conduit element 21 via a detachable connection position 23, a perforation indicated by a broken line in the illustration, provided in the region of the inlet part 5. The conduit elements 21 wound on a supply roll can accordingly each be detached singly from the following conduit element 21. It is understood that the conduit elements 21 can also each be designed with an absorbent wiping edge 19 extending along the inlet part 5 in accordance with the illustration of FIGS. 1 and 2. The conduit elements 21 can also each be provided with at least one transverse fold 16 and be stacked in a single removable manner and foldable around said transverse fold 16, e.g. in a container, not shown, The edge regions 12b and 13b of the second wall parts 2b and 3b can be connected in accordance with the illustration to a correspondingly profiled wall of the second end section B along a connection position with an at least approximately wave-like design. In this way the braking of the urine to be channelled away, which can be achieved in the end section B, is increased and simultaneously a faster soaking of the second end section B achieved.

In accordance with a further embodiment (not shown), the conduit elements 1 and/or 21 can also each be formed by walls executed with two plies and connected to one another at the two side edges. Furthermore, the conduit element 1 can be connected to adjacent conduit elements 1 via connection positions 23.

What is claimed is:

1. A flat-foldable, water-dissolvable urinary aid, comprising a hose-shaped conduit element formed of two walls which lie flatly on one another in a folded condition of the urinary aid and which are made from a softenable and decomposable in water material; and a gripping part connected with the conduit element, wherein the two walls have respective first wall parts forming a first end section with an inlet part positionable at a body part of a user, and have respective second wall parts forming a second end section defining a conduit channel extending from the inlet part to an outlet part provided at an end of the conduit channel remote from the inlet part, wherein inner sides of the first wall parts are provided with a wetting-inhibiting coating over a substantial portion thereof, and inner sides of the second wall parts are free from the wetting-inhibiting coating, wherein the gripping part protrudes sidewise at the first end section, and wherein the first wall parts (2a and 3a) have a wiping edge (19) extending along the inlet part (5) and free of wetting-inhibiting coating.

2. A flat-foldable, water-dissolvable urinary aid, comprising a hose-shaped conduit element formed of two walls which lie flatly on one another in a folded condition of the urinary aid and which are made from a softenable and decomposable in water material; and a gripping part connected with the conduit element, wherein the two walls have respective first wall parts forming a first end section with an inlet part positionable at a body part of a user, and have respective second wall parts forming a second end section defining a conduit channel extending from the inlet part to an outlet part provided at an end of the conduit channel remote from the inlet part, wherein inner sides of the first wall parts are provided with a wetting-inhibiting coating over a substantial portion thereof, and inner sides of the second wall parts are free from the wetting-inhibiting coating, wherein the gripping part protrudes sidewise at the first end section, wherein the gripping part (7) has a form of a pistol grip which is formed by tongue-like protrusions (12) of the first wall parts (2*a* and 3*a*).

3. A flat-foldable, water-dissolvable urinary aid, comprising a hose-shaped conduit element formed of two walls which lie flatly on one another in a folded condition of the urinary aid and which are made from a softenable and decomposable in water material; and a gripping part connected with the conduit element, wherein the two walls have respective first wall parts forming a first end section with an inlet part positionable at a body part of a user, and have respective second wall parts forming a second end section defining a conduit channel extending from the inlet part to an outlet part provided at an end of the conduit channel remote from the inlet part, wherein inner sides of the first wall parts are provided with a wetting-inhibiting coating over a substantial portion thereof, and inner sides of the second wall parts are free from the wetting-inhibiting coating, wherein the gripping part protrudes sidewise at the first end section, and wherein the first and second wall parts (2*a* and 3*a* or 2*b* and 3*b* respectively) are formed by segments of at least one respective one-piece wall part (7, 8, 22) which are designed to fold around a longitudinal fold (10) orientatable in a longitudinal direction of the conduit element (1; 21) and which are connected to one another via edge regions (12*a* and 13*a* or 12*b* and 13*b*, respectively) of the one-piece wall part (7, 8; 22) each extending at a distance from the longitudinal fold (10).

4. An aid in accordance with claim 3, wherein the edge regions (12*b* and 13*b*) of the second wall parts (2*b* and 3*b*) are connected with one another to form a correspondingly sectioned wall section of the conduit element (21) along a connection position formed at least approximately in a wave-like manner.

5. A flat-foldable, water-dissolvable urinary aid, comprising a hose-shaped conduit element formed of two walls which lie flatly on one another in a folded condition of the urinary aid and which are made from a softenable and decomposable in water material; and a gripping part connected with the conduit element, wherein the two walls have respective first wall parts forming a first end section with an inlet part positionable at a body part of a user, and have respective second wall parts forming a second end section defining a conduit channel extending from the inlet part to an outlet part provided at an end of the conduit channel remote from the inlet part, wherein inner sides of the first wall parts are provided with a wetting-inhibiting coating over a substantial portion thereof, and inner sides of the second wall parts are free from the wetting-inhibiting coating, wherein the gripping part protrudes sidewise at the first end section, and wherein the wetting-inhibiting coating (18) of the first wall parts (2*a* and 3*a*) includes a medical test agent reacting to a certain property of urine of a user.

* * * * *